US00PP37369P2

(12) United States Plant Patent
Hansen

(10) Patent No.: US PP37,369 P2
(45) Date of Patent: Apr. 14, 2026

(54) ***HIBISCUS* PLANT NAMED 'Garnet Globes'**

(50) Latin Name: ***Hibiscus hybrid* (L.)**
Varietal Denomination: Garnet Globes

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 4 days.

(21) Appl. No.: 18/831,464

(22) Filed: Jan. 29, 2025

(51) Int. Cl.
*A01H 5/02* (2018.01)
*A01H 5/12* (2018.01)
*A01H 6/60* (2018.01)

(52) U.S. Cl.
USPC ..... Plt./257
CPC ..... *A01H 6/608* (2018.05); *A01H 5/02* (2013.01); *A01H 5/12* (2013.01)

(58) Field of Classification Search
USPC ..... Plt./257
CPC ..... A01H 6/608; A01H 5/02
See application file for complete search history.

*Primary Examiner* — Keith O. Robinson

(57) ABSTRACT

A new and distinct cultivar of winter-hardy, herbaceous, perennial, hybrid *Hibiscus* plant named 'Garnet Globes' comprising a rounded, compact, mound habit of multiple, well-branched, basal stems producing flowers beginning in late July to early August and continuing for at least ten weeks. The flowers are garnet-red colored and open up to produce a flat face with furrows or folding at the veins providing greater strength to withstand wind and rain. The foliage is three-lobed to five-lobed with the divisions cut nearly to the petiole or midrib. The new plant is useful in the landscape as a specimen or in mass.

2 Drawing Sheets

Botanical classification: *Hibiscus* hybrid (L.).
Variety denomination: 'Garnet Globes'.

STATEMENT REGARDING PRIOR DISCLOSURES UNDER 37 CFR 1.77(B)(6)

The first offer for sales was by Walters Gardens, Inc on Feb. 5, 2024. Walters Gardens, Inc. obtained the new plant and all information relating thereto, from the inventor. No plants of *Hibiscus* 'Garnet Globes' have been sold, in this country or anywhere in the world, by any name, nor has any disclosure of the new plant been made more than one year prior to the filing date of this application, and such sale or disclosure within one year was either derived directly or indirectly from the inventor and would be a 35 U.S.C. § 102(b) exception.

BACKGROUND AND ORIGIN OF THE PLANT

The present invention relates to the new and distinct hardy, herbaceous, *Hibiscus* plant, *Hibiscus* 'Garnet Globes' hybridized under the direction of the inventor on Aug. 13, 2020, at a wholesale perennial nursery in Zeeland, Michigan. The new plant is a single seedling selection from the controlled cross between the unreleased, proprietary hybrid known as 19-313-2 (not patented) as the female or seed parent and the unreleased, proprietary hybrid known as 19-334-2 (not patented) as the male or pollen parent. During the trial process, the new plant was assigned the breeder code labeled 20-146-1. The parents have a complex mixture of species in them, believed to be comprising the species: *coccineus, moscheutos, lasiocarpos*, and *grandiflora*.

*Hibiscus* 'Garnet Globes' was first asexually propagated in the late summer of 2021 by sterile shoot-tip tissue culture and later by shoot-tip cuttings at the same nursery in Zeeland, MI. The resultant evaluations of the new plants have found both propagation methods to produce stable and true-to-type plants in successive generations of asexual reproduction.

BRIEF SUMMARY OF THE PLANT

*Hibiscus* 'Garnet Globes' differs from its parents as well as all other hardy herbaceous *Hibiscus* known to the applicant in many combined traits. The most similar *Hibiscus* known to the applicant are: 'Blackberry Merlot' U.S. Plant Pat. No. 33,498, 'Cranberry Crush' U.S. Plant Pat. No. 21,984, 'Heartthrob' U.S. Plant Pat. No. 24,760. 'Holy Grail' U.S. Plant Pat. No. 31,478, 'Mars Madness' U.S. Plant Pat. No. 27,838, 'Sultry Kiss' U.S. Plant Pat. No. 22,300, 'Summer in Paradise' U.S. Plant Pat. No. 28,730, 'Valentine Crush' U.S. Plant Pat. No. 35,170, 'Vintage Wine' U.S. Plant Pat. No. 27,839, and 'Watermelon Ruffles' U.S. Plant patent application Ser. No. 18/445,451.

The female parent has a compact habit with dark burgundy foliage, and the flowers are pink. The male parent has a compact habit, dark green foliage, and red flowers.

Table 1 below includes comparisons of the *Hibiscus* cultivars that are closest known to the inventor:

| Hibiscus cultivar | Flower color | Petal eye color | Petal texture | Pollen color |
|---|---|---|---|---|
| 'Blackberry Merlot' | 59A | 187B | slightly bullate and furrowed | 20C to 161C |
| 'Cranberry Crush' | 45A to 46A | 185B | cupped, deeply veined | 18B |

-continued

| | | | | |
|---|---|---|---|---|
| 'Garnet Globes' | 59A | 187B | furrowed at veins | 16B |
| 'Heartthrob' | 187A to 187B | 187A | flat | 164C |
| 'Holy Grail' | 46A | 183B | flat | 10B |
| 'Mars Madness' | 60D to 53C | 53A | flat | 155A to 158A |
| 'Sultry Kiss' | 185B to 185C | 187B | flat | 159C |
| 'Summer in Paradise' | 61B | 53A | furrowed at veins | 8A |
| 'Valentine Crush' | 53B to 53A | N187B to N187C | flat | 10A |
| 'Vintage Wine' | 187C to 187B | 187A to 187B | furrowed at veins | 16B |
| 'Watermelon Ruffles' | 64C to 64D | 53A to 53B and 59A | rippled and folded | 11A |

| Hibiscus cultivar | Flower size | Plant height | Plant width | Leaf shape |
|---|---|---|---|---|
| 'Blackberry Merlot' | 22 cm | 95 cm | 120 cm | tri-lobed |
| 'Cranberry Crush' | 18 cm | 100 cm | 120 cm | tri-lobed |
| 'Garnet Globes' | 15 cm | 102 cm | 110 cm | palmate |
| 'Heartthrob' | 23 cm | 100 cm | 140 cm | ovate |
| 'Holy Grail' | 22 cm | 80 cm | 110 cm | tri-lobed |
| 'Mars Madness' | 18 cm | 135 cm | 180 cm | tri-lobed |
| 'Sultry Kiss' | 26 cm | 150 cm | 140 cm | palmate |
| 'Summer in Paradise' | 25 cm | 175 cm | 150 cm | tri- to penta-lobed |
| 'Valentine Crush' | 22 cm | 145 cm | 155 cm | tri-lobed |
| 'Vintage Wine' | 21 cm | 135 cm | 150 cm | ovate to tri-lobed |
| 'Watermelon Ruffles' | 20 cm | 132 cm | 165 cm | tri- to penta-lobed |

| Hibiscus cultivar | Young leaf color | Mature leaf color |
|---|---|---|
| 'Blackberry Merlot' | 138A with strong 187A to N187A | 139A to NN137A |
| 'Cranberry Crush' | 139A to 139B with N187B to N187A | 139A to 139B with N187B to N187A |
| 'Garnet Globes' | 137B with slight blush 187B | NN137A and NN137B |
| 'Heartthrob' | 137A to 139B | 137A to 139B with margins of 184A |
| 'Holy Grail' | N186C | N186C |
| 'Mars Madness' | 137A blushed 187A | 137A blushed 187A |
| 'Sultry Kiss' | 137A to 137B with tinting N186B to 187A | 137A to 137B with tinting N186B to 187A |
| 'Summer in Paradise' | 137A with blush N187A | 139A to 137A |
| 'Valentine Crush' | NN137B | NN137A |
| 'Vintage Wine' | 139B | 137A with N187A to 187B |
| 'Watermelon Ruffles' | NN137B | NN137A with faint blush 187A |

*Hibiscus* 'Garnet Globes' is a unique hardy herbaceous *Hibiscus* with the following combined traits:

1. Winter-hardy, densely-compact perennial with a rounded mound habit of multiple, well-branched, basal stems;
2. Rotate flowers with highly overlapping petals of garnet red with a slightly darker eye;
3. Flowering beginning in late July to early August and continuing for at least ten weeks;
4. Petals open wide and are furrowed or folded at the veins producing greater strength to withstand wind and rain;
5. Foliage is three to five lobed with divisions cut nearly to petiole or midrib.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source, temperature, and direction may cause the appearance of minor variations in color.

DETAILED BOTANICAL DESCRIPTION

Figure 1:
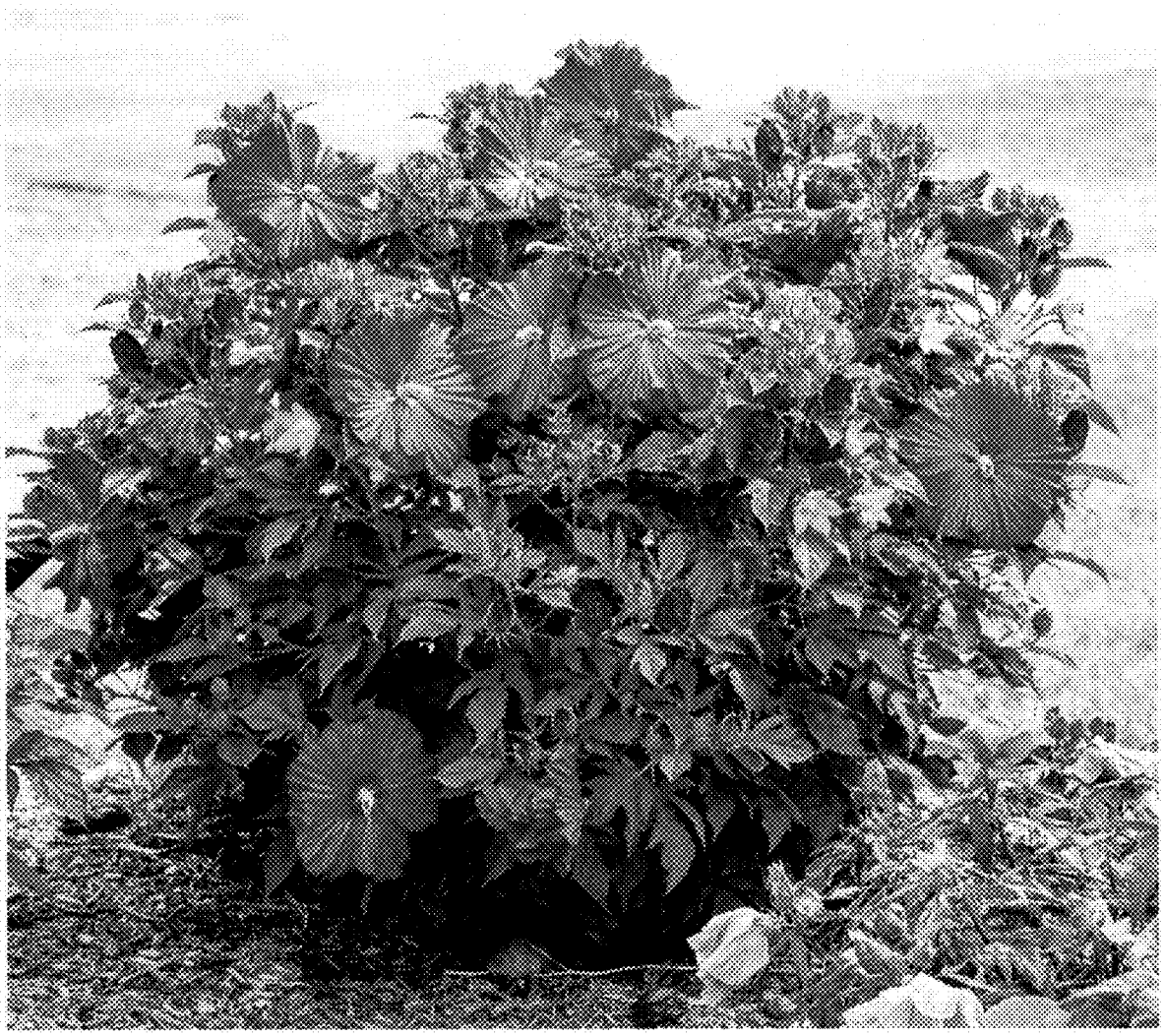
FIG. 1 shows a four-year-old plant in full flower in a display garden.
Figure 2:
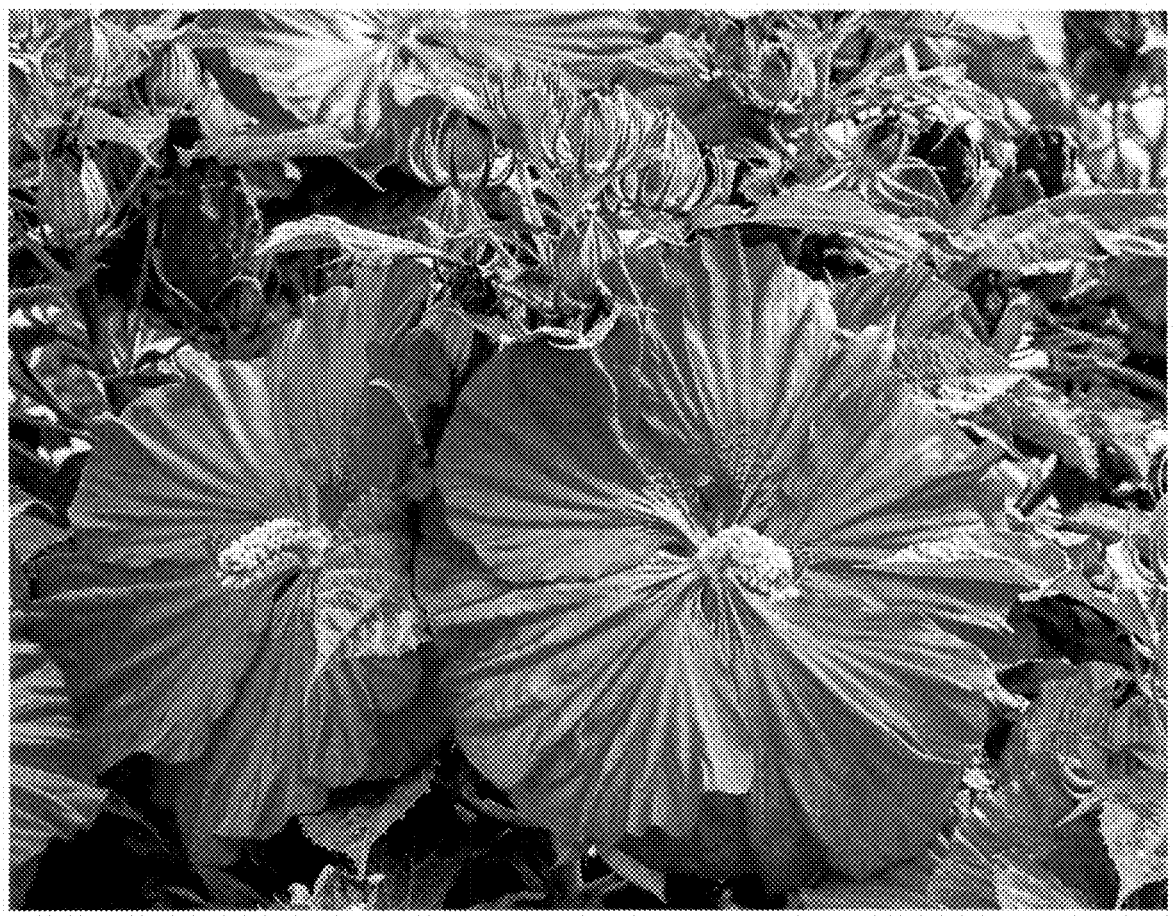
FIG. 2 shows a close-up of some flowers and buds.

The following descriptions and color references are based on the 2015 edition of The Royal Horticultural Society Colour Chart except where common dictionary terms are used. The new plant, *Hibiscus* 'Garnet Globes', has not been observed in all possible environments. The phenotype may vary slightly with different environmental conditions, such as temperature, light, fertility, moisture, and maturity levels, but without any change in the genotype. The following observations and size descriptions are of a three-year-old plant in the loamy-sand, open-field full-sun display garden of a nursery in Zeeland, MI with supplemental fertilizer and water as needed. The plants are of natural habit and were not treated with plant growth regulators, nor were they pinched at any time in the growth year.

Parentage: The female parent is 19-313-2; the male parent is 19-334-2;

Propagation:

*Method*.—Shoot tip cuttings and sterile shoot-tip plant tissue culture division.

*Time to initiate roots from tissue culture*.—About two weeks.

*Rooting habit*.—Normal, branching, developing thick to about 2 cm diameter, fleshy; root color creamy yellow nearest RHS 161D depending on soil type.

*Crop time*.—Under normal summer growing conditions 15 to 18 weeks to flower in a four- liter container from cutting without vernalization; vigor is moderate;

Plant description:

*Plant habit*.—Hardy herbaceous perennial with about 25 thick, upright, lightly branched stems producing a rounded mound to about 102 cm tall and about 110 cm wide; flowering in distal two-thirds of the plant.

*Stem*.—Cylindrical, glabrous, glaucous; to about 100 cm long and about 20 mm diameter at the base, average about 85 cm long and about 17 mm diameter at base; lightly branched.

*Stem color*.—Nearest RHS 146D in portions protected from direct sunlight, between RHS N186D and RHS N77D in regions with higher sunlight exposure.

*Branches*.—To 4 per stem, average about 2 per stem; cylindrical, glabrous, glaucous; to about 32 cm long and 5 mm diameter at base, smaller distally.

*Branch color*.—Nearest RHS 146D in portions protected from direct sunlight, between RHS N186D and RHS N77D in regions with higher sunlight exposure.

*Internode*.—About 20 nodes per stem below unbranched portion; average 41 nodes per stem; internode length about 2 cm of an unpinched plant.

*Internode color*.—Same as surrounding stem.

Foliage description: Palmate; tri-lobed to penta-lobed, with lobes deeply dissected to petiole or midrib or nearly to petiole or midrib; alternate; irregularly dentate; apex and side lobes acute; base cordate; glabrous and matte both abaxial and adaxial;

Leaf blade size: To about 13 cm long and about 10.5 cm across, average blade size 10 cm long and 7.5 cm wide; no fragrance detected;

*Foliage color*.—Young expanding leaves-adaxial nearest RHS 137B with slight marginal blush of nearest RHS 187B, abaxial between RHS 137B and RHS 138A with a slight marginal blush of nearest RHS 187B; mature leaves-adaxial between RHS NN137A and RHS NN137B, abaxial between RHS N148B and RHS 195A.

*Veins*.—Palmate; lustrous adaxial; costate, micro-puberulent, and matte abaxial.

*Vein color*.—Adaxial midrib proximally nearest RHS 187C and distally nearest RHS 187A, primary and secondary veins nearest RHS 187A; abaxial midrib nearest RHS 146D, primary and secondary veins nearest RHS 147C.

*Petioles*.—Mostly cylindrical, proximally slightly applanate on adaxial surface; micro-puberulent; to about 10 cm long and 4 mm across at base, average size about 7 cm long and 3.5 mm wide at base.

*Petiole color*.—Adaxial between RHS 187A and RHS N187A; abaxial between RHS 146D and RHS 144A.

Flower description: Complete; perfect; actinomorphic; rotate; solitary; mostly outwardly facing; moderately cupped; rotate; lasting up to two days on the plant;

Flowering season: Beginning in late July and continuing for at least five weeks;

Flower size: To about 15 cm across natural spread, 7 cm deep, and 16.5 cm across if flattened, decreasing in size slightly in size distally and later in the season;

*Buds one day prior to anthesis*.—Ellipsoidal with rounded apex and bluntly truncate base; sepals adpressed to petals; to about 6.5 cm long and about 4 cm diameter near middle.

*Bud color one day prior to anthesis*.—Exposed petal color main portion between RHS 187C and RHS 59A, calyx abaxial basal portion nearest RHS 146B with distal portion in high light exposure veins nearest RHS 187C.

*Epicalyx*.—Average about 8 per flower; linear; entire, with margin micro-ciliolate; micro-puberulent, dull surfaces both abaxial and adaxial; sharply acute apex and truncate base; arcuate upwards near apex; to about 30 mm long and about 4 mm wide at base.

*Epicalyx color*.—Adaxial base nearest RHS 146A and moderately blushed or maculate with nearest RHS 187C, middle and distal portions between RHS 144A and RHS 146D, abaxial base between RHS 144A and RHS 146D, middle and distal portions nearest RHS 137B with veins nearest RHS 187C.

*Calyx*.—Campanulate, form star-shaped hypanthium; to about 20 mm deep and 40 mm wide at apices.

*Sepals*.—Typically, five; ovate; acute to apiculate apex; margin entire, edentate; adaxial and abaxial micro-puberulent and matte; about 30 mm long, about 18 mm wide at fusion, basal 10 mm fused.

*Sepal color*.—Adaxial basal portion nearest RHS 146D blushed lightly with nearest RHS 187C; abaxial proximally between RHS 144A and RHS 146D, strongly blushed to solid nearest RHS 187A in the distal one-half to one third.

*Inflorescence*.—Up to 46 per main stem and branches without pinching; single flower per node.

*Flower lastingness*.—Persist for one to two days; effective beginning late July or early August and lasting for at least 5 weeks.

*Flower fragrance*.—None detected.

*Petals*.—Five; glabrous adaxial and abaxial; adaxial eye zone of about the proximal 15 mm lustrous, remaining distal adaxial portion and entire abaxial matte; adnate to the androecium to form a column, imbricate to about 110% overlapping at widest part (petals overlapping both petals on either side, so two petals about 10% overlapping a third petal); margin undulation slight; with inside leading edge of petals frequently folded or pleated about 4 mm; palmately veined, primary veins slightly impressed on adaxial and costate abaxial; surface slightly rippled along veins; apex rounded with distinct basal claw and limb; margins entire, edentate.

*Petal size*.—To about 12 cm across including folded portion and about 8.5 cm long, claw base about 9 mm across.

*Petal color*.—Adaxial basal eye highly lustrous nearest RHS 187B, distal portion toward margin nearest RHS 59A, region between slightly lighter between RHS 60A and RHS 59A; with veins same color as surround region; abaxial proximal 2 mm of claw nearest RHS NN155C, surrounding eye to about 8 mm from claw base between RHS 61C and RHS 61B, distally between RHS 59A and RHS 60A.

*Flower lastingness*.—One to two days.

*Gynoecium*.—Single; partially enclosed in column. Column: glabrous and lustrous; terete, fistulous; about 35 mm long and about 11 mm across at base; with pistil exserted about 12 mm. Column color: between RHS 60D and RHS NN155D. Style: micro-puberulent in region exserted above column; about 50 mm long, penta-furcate in about distal 7 mm, branch diameter about 1 mm; color nearest RHS NN155B in exposed portion, and RHS NN155B portion enclosed in column. Stigma: five; spheroid flattened proximally and distally; puberulent; about 3 mm in diameter and 1 mm tall; color between RHS 53A and RHS 60A. Ovary: superior; conical with a acute apex and truncate base; longitudinally grooved in undulated pattern; about 11 mm across at base and about 10 mm tall; color nearest RHS 150D.

*Androecium*.—Attached to column. Filaments: numerous, about 125, attached starting about 12 mm from base to 2 mm from apex of column; to about 3 mm long, about 0.3 mm diameter; color nearest RHS 60C. Anthers: flattened reniform; dorsifixed; about 2 mm across, 2.5 mm long, and about 1 mm thick; color variable, proximal anthers nearest RHS 10D on sides with a light blush of nearest RHS 60C, distal anthers nearest RHS 10D throughout. Pollen: abundant, globose, less than 0.2 mm across; color nearest RHS 16B.

Pedicel: Cylindrical; glabrous; lightly glaucous; length from base of sepal to abscission point to about 17 mm long, from abscission point to stem node to about 85 mm long; about 4 mm wide; longer on early flowers and decreasing in distal flowers;

Pedicel color: Between RHS N144D and RHS 145A in ventral portion away from the sun, and nearest RHS 183C with an undertone of nearest RHS NN144A in the dorsal portion;

Peduncle: Cylindrical; glabrous; glaucous; flowering in upper 65 cm; to about 60 cm tall and about 12 mm diameter from below unbranched portion; to about 32 flowers per center main stem, to 5 flowers per branch, and 46 flowers on the whole stem;

Peduncle color: nearest RHS 146D in portions protected from direct sunlight, between RHS N186D and RHS N77D in regions with higher sunlight exposure;

Fruit: Rare; penta-loculicidal capsule; with pubescent along inner septa; puberulent outside; ellipsoidal, cuspidate apex and truncate base; about 20 mm tall and 18 mm diameter; color nearest RHS 200A when mature; about 85 seeds per fruit;

Seed: Minutely hispidulous; globose; about 3.5 mm in diameter; color between RHS 200C and RHS 200D;

Resistance: *Hibiscus* 'Garnet Globes' has not displayed any pest and disease resistance or susceptibility beyond that typical of hardy perennial *Hibiscus*.

Growth: The new plant grows best with plenty of moisture.

Hardiness: At least from USDA zone 4 through 9.

I claim:

1. A new cultivar of hardy herbaceous perennial *Hibiscus* hybrid plant named 'Garnet Globes' as herein illustrated and described.

* * * * *